United States Patent
Lee et al.

(10) Patent No.: US 10,322,015 B2
(45) Date of Patent: Jun. 18, 2019

(54) MOTION ASSISTANCE APPARATUS AND CONTROL METHOD OF THE SAME

(71) Applicant: Samsung Electronics Co., Ltd., Suwon-si, Gyeonggi-do (KR)

(72) Inventors: Minhyung Lee, Seoul (KR); Jeonghun Kim, Hwaseong-si (KR); Se-Gon Roh, Suwon-si (KR); Youn Baek Lee, Yongin-si (KR); Jongwon Lee, Suwon-si (KR); Byungjune Choi, Gunpo-si (KR); Hyun Do Choi, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 629 days.

(21) Appl. No.: 15/145,208

(22) Filed: May 3, 2016

(65) Prior Publication Data

US 2017/0065441 A1 Mar. 9, 2017

(30) Foreign Application Priority Data

Sep. 4, 2015 (KR) .................. 10-2015-0125698

(51) Int. Cl.
*A61F 2/68* (2006.01)
*A61F 3/00* (2006.01)
(Continued)

(52) U.S. Cl.
CPC .............. *A61F 2/72* (2013.01); *A61B 5/1072* (2013.01); *A61B 5/112* (2013.01); *A61B 5/6812* (2013.01);
(Continued)

(58) Field of Classification Search
CPC .......... A61F 2/72; A61F 2/70; A61H 1/0262; A61H 3/00; A61H 1/0237; A61H 2003/007; B25J 9/0006
(Continued)

(56) References Cited

U.S. PATENT DOCUMENTS

| 7,416,538 B2 | 8/2008 | Katoh et al. |
| 7,780,616 B2 | 8/2010 | Katoh et al. |

(Continued)

FOREIGN PATENT DOCUMENTS

| JP | 4071755 B2 | 4/2008 |
| JP | 2009284919 A | 12/2009 |

(Continued)

OTHER PUBLICATIONS

Jia-fan, Z., et al. "5-Link Model Based Gait Trajectory Adaption Control Strategies of the Gait Rehabilitation Exoskeleton for Post-stroke Patients". Mechatronics 20 (2010): 368-376. (Year: 2010).*

*Primary Examiner* — Brian E Pellegrino
*Assistant Examiner* — Rebecca Lynee Zimmerman
(74) *Attorney, Agent, or Firm* — Harness, Dickey & Pierce, P.L.C.

(57) ABSTRACT

A motion assistance apparatus including a fixing module attached to a user, a driving module fixed to the fixing module to generate rotation power, a supporting module configured to support a portion of a body of the user and driven by the driving module, a sensor configured to measure a width of the fixing module, and a controller configured to adjust the rotation power of the driving module based on the measured width.

12 Claims, 13 Drawing Sheets

(51) Int. Cl.
  *A61F 2/60* (2006.01)
  *A61F 2/72* (2006.01)
  *A61F 2/70* (2006.01)
  *A61B 5/11* (2006.01)
  *A61H 3/00* (2006.01)
  *A61H 1/02* (2006.01)
  *B25J 9/00* (2006.01)
  *B25J 13/08* (2006.01)
  *A61B 5/107* (2006.01)
  *A61B 5/00* (2006.01)

(52) U.S. Cl.
  CPC ............. *A61F 2/70* (2013.01); *A61H 1/0255* (2013.01); *A61H 3/00* (2013.01); *B25J 9/0006* (2013.01); *B25J 13/087* (2013.01); *A61H 2201/0192* (2013.01); *A61H 2201/1215* (2013.01); *A61H 2201/1463* (2013.01); *A61H 2201/164* (2013.01); *A61H 2201/165* (2013.01); *A61H 2201/1628* (2013.01); *A61H 2201/1676* (2013.01); *A61H 2201/5007* (2013.01); *A61H 2201/5061* (2013.01); *A61H 2201/5064* (2013.01); *A61H 2230/80* (2013.01); *A61H 2230/82* (2013.01); *A61H 2230/85* (2013.01)

(58) Field of Classification Search
  USPC .......... 248/332; 623/48; 602/24; 601/33, 34, 601/71; 128/882; 600/202; 606/263, 606/151
  See application file for complete search history.

(56) References Cited

U.S. PATENT DOCUMENTS

| | | |
|---|---|---|
| 8,652,075 B2 | 2/2014 | Takahashi et al. |
| 8,784,344 B2 | 7/2014 | Takahashi et al. |
| 2012/0310122 A1 | 12/2012 | Endo et al. |
| 2016/0113831 A1* | 4/2016 | Hollander ............ A61H 1/0244 623/31 |

FOREIGN PATENT DOCUMENTS

| | | |
|---|---|---|
| JP | 2012-143449 A | 8/2012 |
| JP | 5081740 B2 | 11/2012 |
| JP | 2014184086 A | 10/2014 |
| KR | 101146112 B1 | 5/2012 |
| KR | 101417895 B1 | 7/2014 |

* cited by examiner

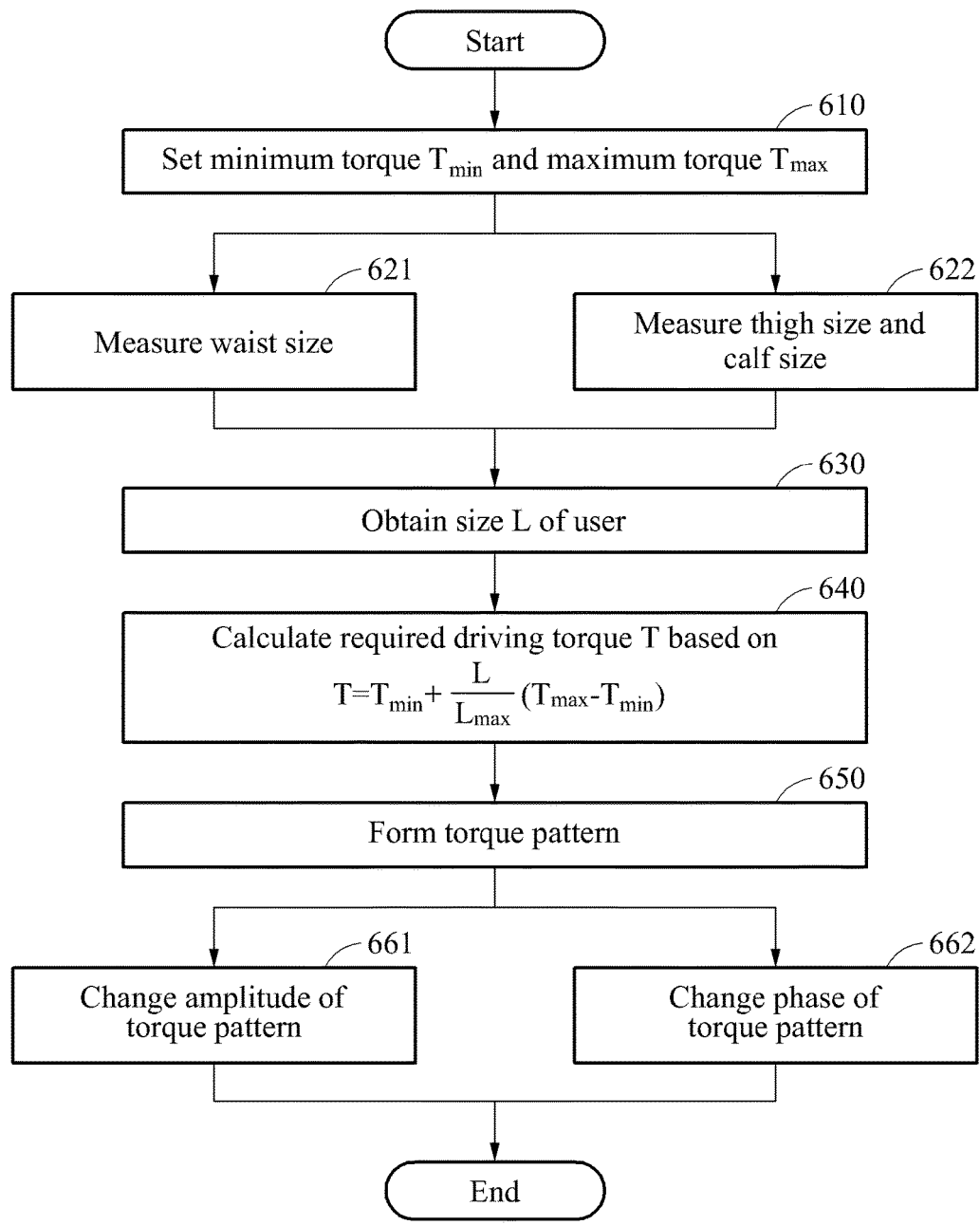

MOTION ASSISTANCE APPARATUS AND CONTROL METHOD OF THE SAME

CROSS-REFERENCE TO RELATED APPLICATION

This application claims under 35 U.S.C. § 119 to Korean Patent Application No. 10-2015-0125698, filed on Sep. 4, 2015, at the Korean Intellectual Property Office, the entire contents of which are incorporated herein by reference in its entirety.

BACKGROUND

1. Field

At least one example embodiment relates to a motion assistance apparatus and/or a control method of the motion assistance apparatus.

2. Description of the Related Art

With the onset of rapidly aging societies, many people may experience inconvenience and pain from joint problems, and interest in walking assistance apparatuses enabling the elderly or patients with joint problems to walk with less effort, may increase. Furthermore, walking assistance apparatuses for intensifying muscular strength of human bodies may be useful for military purposes.

SUMMARY

Some example embodiments relate to a motion assistance apparatus.

In some example embodiments, the motion assistance apparatus includes a fixing device attached to a user; a driver configured to generate rotation power; a support configured to support a portion of a body of the user and rotate in response to the rotation power; a sensor configured to measure a width of the fixing device; and a controller configured to adjust the rotation power based on the measured width.

In some example embodiments, the rotation power includes a driving torque transmitted from the driver to the support, and the controller is configured to determine the driving torque between a minimum driving torque and a maximum torque based on the measured width.

In some example embodiments, the controller is configured to determine the driving torque based on:

$$T = T_{min} + \frac{W}{W_{max}} \cdot (T_{max} - T_{min})$$

where T denotes the driving torque, $T_{min}$ denotes the minimum driving torque, $T_{max}$ denotes the maximum driving torque, W denotes the width of the fixing device, and $W_{max}$ denotes a maximum width of the fixing device.

In some example embodiments, the controller is configured to set an amplitude of a torque pattern between the minimum torque Tmin and the maximum torque Tmax, and apply the set torque pattern as the driving torque.

In some example embodiments, the fixing device comprises: a width adjuster configured to adjust the width of the fixing device, wherein the sensor is connected to the width adjuster.

In some example embodiments, the fixing device includes a first side frame configured to enclose a first side of the user and a second side frame configured to enclose a second side of the user, and the width adjuster includes a fixing knob configured to fix the first side frame and the second side frame by passing through a first slot and a second slot in the first side frame and the second side frame, respectively such that the width of the fixing device decreases according to an increase in an overlapping portion between the first side frame and the second side frame.

In some example embodiments, the sensor comprises: a linear potentiometer including, a variable resistor having a first side and a second side, the first side connected to the controller and the second side connected to one of the first side frame and the second side frame, and a magnetic body connected to the fixing knob, the magnetic body configured to change a resistance value of the variable resistor based on a location of the magnetic body.

In some example embodiments, the variable resistor is connected to the one of the first side frame and the second side frame and the magnetic body is connected to the fixing knob such that the variable resistor and the magnetic body are on one side of the first slot and the second slot, respectively.

In some example embodiments, the sensor comprises: a linear variable differential transformer (LVDT) sensor including, a core connected to the fixing knob, and a main body connected to one of the first side frame and the second side frame, the main body configured to transmit width data to the controller.

In some example embodiments, the core is configured to move relative to the main body such that a penetration amount the core penetrates the main body varies based on a width of the fixing device, and the main body is configured generate the width data based on the penetration amount.

Some other example embodiments also relate to a motion assistance apparatus.

In some example embodiments, the motion assistance apparatus includes a fixing device configured to attach to a first portion of a user; a driver rotatably connected to the fixing device; a support configured to support a second portion of the user and be driven by the driver; a sensor configured to measure at least a first size associated with the first portion of the user and a second size associated with the second portion of the user; and a controller configured to adjust rotation power of the driver based on the first size and the second size.

In some example embodiments, the sensor comprises: a first sensor included in the fixing device to measure the first size; and a second sensor included in the support to measure the second size.

In some example embodiments, the controller is configured to, determine a total user size based on the first size and the second size, and determine a driving torque associated with the rotation power based on the following equation:

$$T = T_{min} + \frac{L}{L_{max}} \cdot (T_{max} - T_{min})$$

where T denotes the driving torque, $T_{min}$ denotes a minimum driving torque, $T_{max}$ denotes a maximum driving torque, L denotes the total user size, and $L_{max}$ denotes a maximum total user size.

In some example embodiments, the first sensor comprises: a plurality of location sensors arranged along a circumference of the fixing device, the plurality of waist location sensors configured to transmit location information associated therewith to the controller, and wherein the controller is configured to measure a waist size of the user based on the location information.

In some example embodiments, the support comprises: a supporting frame including a plurality of joints configured to spread apart or press together to support the second portion of the user, wherein the second sensor includes a plurality of leg location sensors along a circumference of the supporting frame.

In some example embodiments, the supporting frame comprises: a thigh supporting frame configured to support a thigh part of the user and a calf supporting frame configured to support a calf part of the user, wherein the plurality of leg location sensors are along a circumference of the thigh supporting frame and the calf supporting frame.

In some example embodiments, the supporting frame comprises: the plurality of joints configured to cover a portion of the user; a wire fixed to an end portion of the plurality of joints by passing through an inside thereof; and an adjusting device configured to wind and unwind the wire.

In some example embodiments, when the user wears the supporting frame, the controller is configured to control the adjusting device such that the second portion of the user is automatically bound to the joint portion, and the controller is configured to measure a size of the second portion of the user using the plurality of leg location sensors while the second portion of the user is bound to the supporting frame.

Some example embodiments relate to a method of controlling a motion assistance apparatus.

In some example embodiments, the method includes measuring, by a sensor associated with a fixing device attached to a first portion of the user, a width of the fixing device; and adjusting, by a controller, a rotation power of a driver based on the measured width, the driver configured to drive a support configured to support a second portion of the user.

In some example embodiments, the adjusting comprises: determining the rotation power based on the following equation:

$$T = T_{min} + \frac{W}{W_{max}} \cdot (T_{max} - T_{min})$$

where T denotes a driving torque associated with the rotation power, $T_{min}$ denotes a minimum driving torque, $T_{max}$ denotes a maximum driving torque, W denotes the measured width of the fixing device, and $W_{max}$ denotes a maximum width of the fixing device.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which:

FIG. 12 is a flowchart illustrating another example of a method of controlling a motion assistance apparatus.

DETAILED DESCRIPTION

Figure 1:
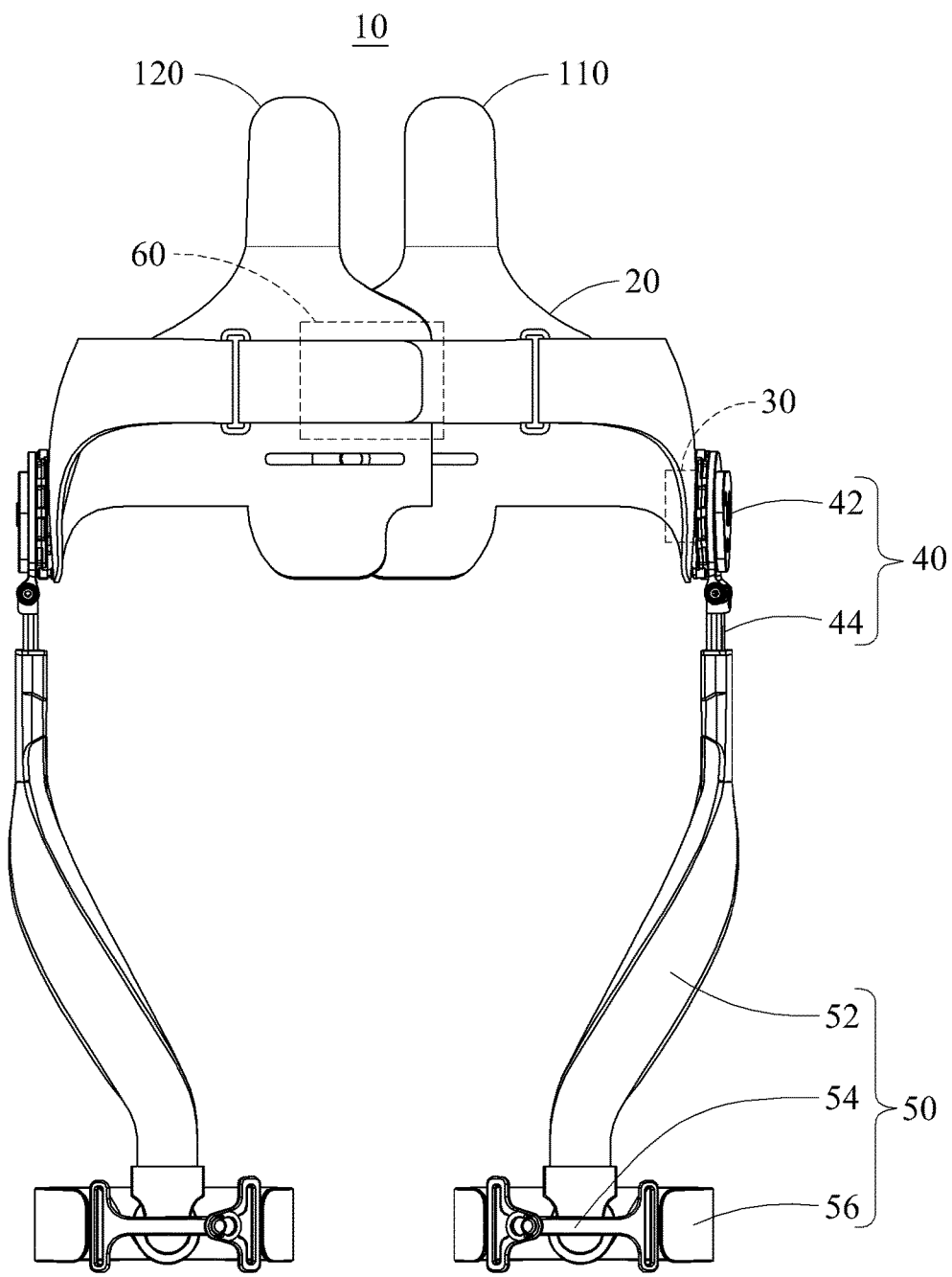
FIG. 1 is a front view illustrating an example of a motion assistance apparatus according to some example embodiments.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as one computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

Various example embodiments will now be described more fully with reference to the accompanying drawings in which some example embodiments are shown. In the drawings, the thicknesses of layers and regions are exaggerated for clarity.

Figure 2:
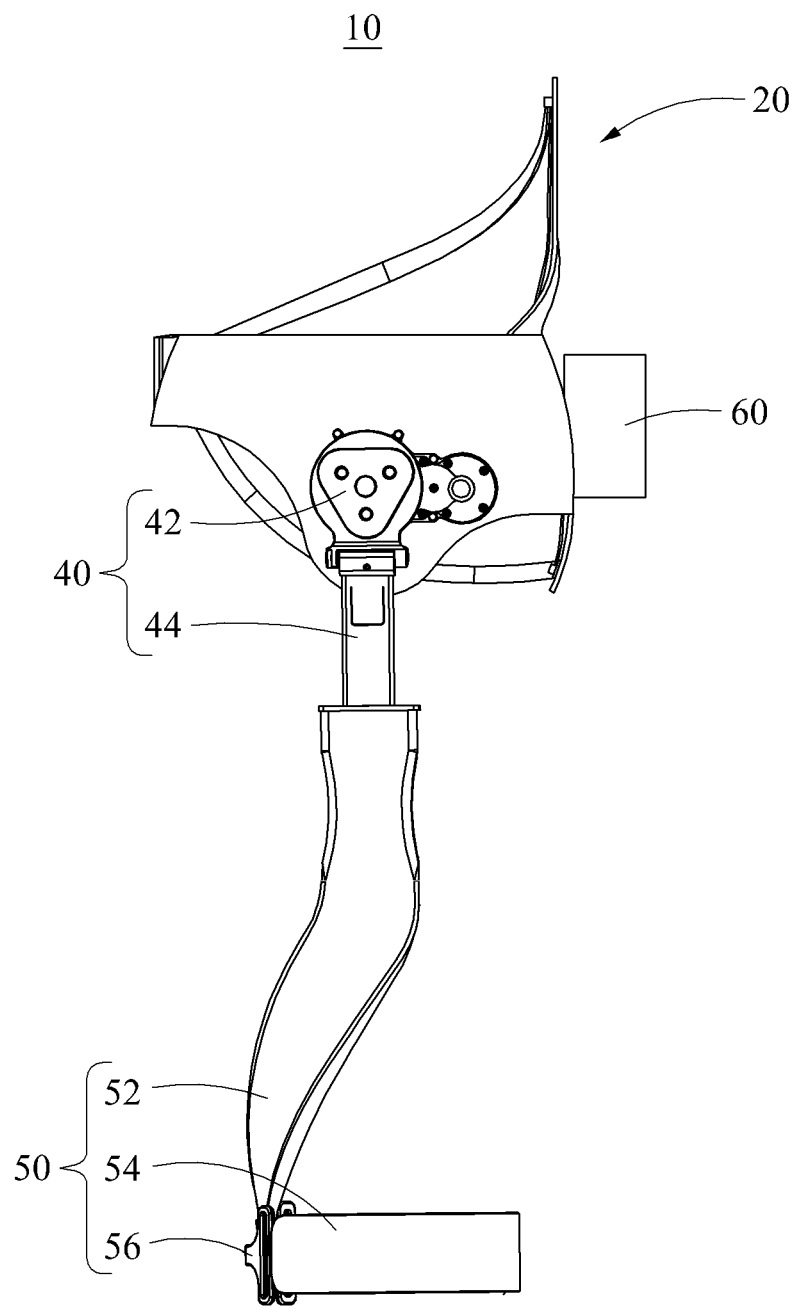
FIG. 2 is a side view illustrating an example of a motion assistance apparatus.

FIG. 1 is a front view illustrating a motion assistance apparatus and FIG. 2 is a side view illustrating the motion assistance apparatus according to some example embodiments.

Referring to FIGS. 1 and 2, a motion assistance apparatus 10 may be worn by a user to assist a motion of the user.

The user may be a human, an animal, or a robot. However, example embodiments are not limited thereto. Further, although FIG. 1 illustrates a case in which the motion assistance apparatus 10 assists a motion of a thigh of the user, the motion assistance apparatus 10 may also assist a motion of another part of an upper body, for example, a hand, an upper arm, and a lower arm of the user, or a motion of another part of a lower body, for example, a foot, and a calf of the user. The motion assistance apparatus 10 may assist a motion of a part of the user.

Hereinafter, a case in which the motion assistance apparatus 10 assists a motion of a thigh of a human will be described as an example.

The motion assistance apparatus 10 may include a fixing module 20, a driving module 30, a joint assembly 40, a supporting module 50, and a controller 60.

The fixing module 20 may be attached to the user, and configured to cover an external surface of the user. For example, the fixing module 20 may be attached to one side of a waist of the user, and include a curved surface corresponding to a contact portion of the user. The fixing module 20 may include a first side frame 110 disposed on one side of the user and a second side frame 120 disposed on another side of the user.

The driving module 30 may provide power to be transmitted to the joint assembly 40. For example, the driving module 30 may be disposed in a lateral direction of the joint assembly 40, in detail, such that an axis of rotation of the driving module 30 may be spaced apart from an axis of rotation of the joint assembly 40. In this example, when compared to a case in which the driving module 30 and the joint assembly 40 share an axis of rotation, a height of a portion protruding from the user may relatively decrease. The driving module 30 may be disposed to be spaced apart from the joint assembly 40 much more than is illustrated in the drawings. In this example, a power transmitting module may be additionally provided to transmit power from the driving module 30 to the joint assembly 40. The power transmitting module may be a rotary body such as, for example, a gear, or a longitudinal member such as, for example, a wire, a cable, a string, a rubber band, a spring, a belt, and a chain.

The joint assembly 40 may receive power from the driving module 30, and assist a motion of a joint portion of the user. The joint assembly 40 may be disposed on one side of the fixing module 20 at a position corresponding to the joint portion of the user. One side of the joint assembly 40 may be connected to the driving module 30, and another side of the joint assembly 40 may be connected to the supporting module 50.

The joint assembly 40 may include a rotating member 42, and a connecting member 44. The rotating member 42 may rotate using power received from the driving module 30. For example, the rotating member 42 may be disposed on one side of a hip joint of the user. The connecting member 44 may connect the rotating member 42 to the supporting module 50, and rotate using torque of the rotating member 42. The connecting member 44 may be provided, for example, in a hinge connection structure. By a hinge axis of the hinge connection structure and an axis of rotation of the rotating member 42, the supporting module 50 may perform a two degree of freedom (DOF) motion with respect to the fixing module 20.

The supporting module 50 may include a supporting frame 52, an applying member 54, and a supporting band 56.

The supporting module 50 may support a portion of the user, and assist a motion of the portion of the user, for example, the supporting module 50 may be configured to rotate using torque of the joint assembly 40.

The supporting frame 52 may transmit force to a portion of the user. One end portion of the supporting frame 52 may be rotatably connected to the joint assembly 40, and another end portion of the supporting frame 52 may be connected to the supporting band 56 to transmit force to a portion of the user. For example, the supporting frame 52 may push or pull a thigh of the user. The supporting frame 52 may extend and be bent in a longitudinal direction of the thigh of the user to cover at least a portion of the circumference of the thigh of the user. The one end portion of the supporting frame 52 may be disposed on a side surface of the thigh of the user, and the other portion of the supporting frame 52 may be disposed on a front surface of the thigh of the user. A surface on the side of the one end portion of the supporting frame 52 may be orthogonal to a surface on the side of the other end portion of the supporting frame 52.

The supporting frame 52 may be movably connected to the connecting member 44. By relative motions of the supporting frame 52 and the connecting member 44, a total length from the joint assembly 40 to the supporting band 56 may be variable. In this example, the supporting module 50 may perform a three DOF motion with respect to the fixing module 20.

The applying member 54 may be connected to the other end portion of the supporting frame 52 to apply force to a portion of the user. For example, the applying member 54 may be disposed along the front surface of the thigh of the user, or in a circumferential direction of the thigh of the user to push or pull the thigh of the user. The applying member 54 may include a curved surface corresponding to the thigh of the user, and configured to extend from the other end portion of the supporting frame 52 toward both sides of the supporting frame 52.

The supporting band 56 may be connected to one side of the applying member 54. For example, the supporting band 56 may be disposed to cover a circumference of at least a portion of the thigh of the user, thereby preventing separation between the thigh of the user and the supporting frame 52.

Figure 3:
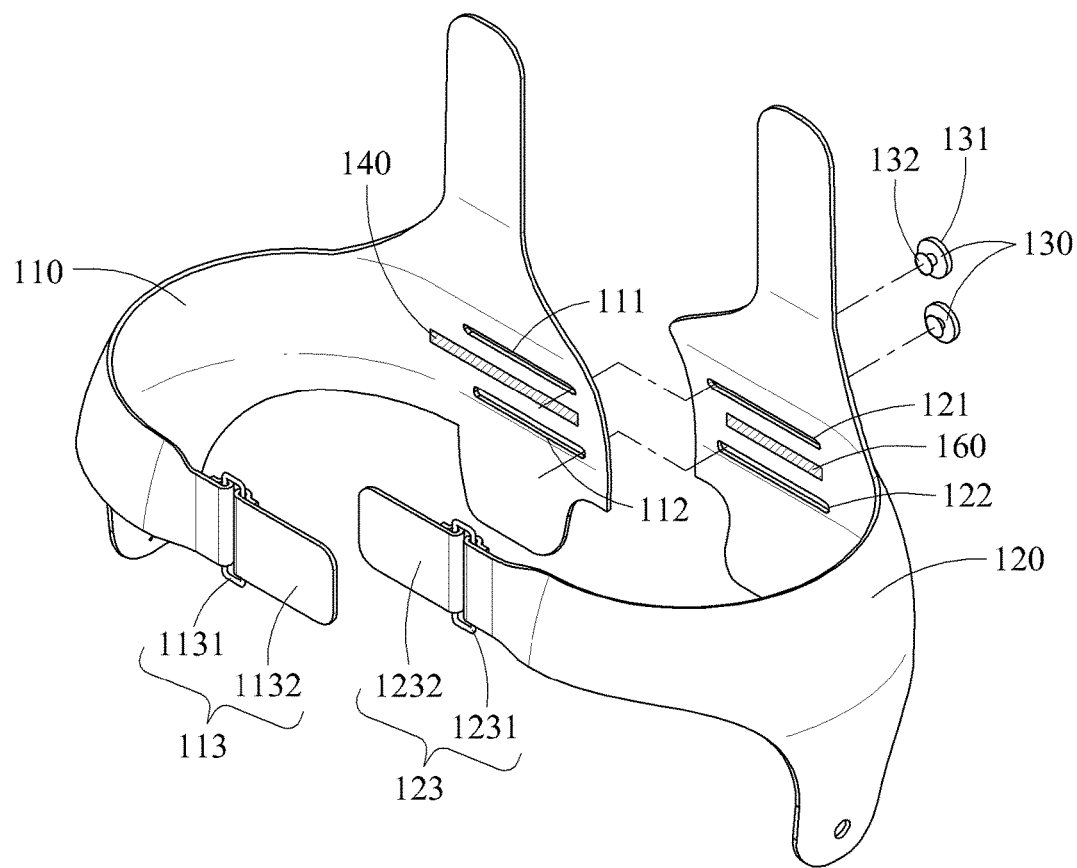
FIG. 3 is a perspective view illustrating an example of a fixing module including a linear potentiometer.

FIG. 3 is a perspective view illustrating a fixing module including a linear potentiometer.

Referring to FIG. 3, the fixing module 20 may include a linear potentiometer 140. In general, a waist width of a user may be proportional to a weight of the user, and the desired amount of torque provided to assist the user may also vary based on the weight of the user. Thus, a driving torque of the driving module 30 may be adjusted by measuring a width of the fixing module 20.

As an example, when a user is pregnant or suffers from abdominal obesity, a required intensity of driving torque may be less than that of a common user despite a relatively large waist width. As another example, when a user has muscle mass greater than that of a common user, a required intensity of driving torque may be greater than that of the common user despite a relatively slight increase in waist width. Thus, a degree to which a driving torque is proportional to a waist width may be differently set based on a condition of a user.

The fixing module 20 may include the first side frame 110 provided on a left side and the second side frame 120 provided on a right side. A first front extender 113 may be disposed in a front portion of the first side frame 110. The first front extender 113 may be configured to be attached to or detached from the second side frame 120 in front of the user.

The first front extender 113 may be extended from a center portion of the first side frame 110 to cover at least a portion of a front surface of the user. The first front extender 113 may include a first binder 1131 provided in a buckle structure and a first connector 1132 provided in a hook-and-loop structure.

A second front extender 123 may be disposed in a front portion of the second side frame 120. The second front extender 123 may be configured to be attached to or detached from the first side frame 110 in front of the user. The second front extender 123 may be extended from a center portion of the second side frame 120 to cover at least a portion of the front surface of the user. The second front extender 123 may include a second binder 1231 provided in the buckle structure and a second connector 1232 provided in the hook-and-loop structure.

A first slot may be formed in a rear portion of the first side frame 110 covering a portion of the waist corresponding to a back part of the user. The first slot may include the first upper slot 111 and a first lower slot 112. The first upper slot 111 and the first lower slot 112 may be provided in a form of which a horizontal length is greater than a vertical length.

The linear potentiometer 140 may be disposed between the first upper slot 111 and the first lower slot 112. The linear potentiometer 140 may be configured to function as a sensor to measure a width of the fixing module 20. The linear potentiometer 140 may also be disposed above the first upper slot 111. Alternatively, the linear potentiometer 140 may also be disposed under the first lower slot 112.

A second slot may be disposed in a rear portion of the second side frame 120 covering a portion of the waist corresponding to a back part of the user. The second slot may include a second upper slot 121 and a second lower slot 122. The second upper slot 121 may be provided in a form substantially the same as that of the first upper slot 111 and parallel with the first upper slot 111. Also, the second lower slot 122 may be provided in a form substantially the same as that of the first lower slot 112 and parallel with the first lower slot 112.

In some example embodiments, a second linear potentiometer 160 may be additionally provided between the second upper slot 121 and the second lower slot 122 of the second side frame 120.

The first slot may be bound to the second slot with a fixing knob 130. The fixing knob 130 may include a handle 131 at one end and an insert 132 at another end. The fixing knob 130 may include an upper fixing knob configured to bind the first upper slot 111 and the second upper slot 121 and a lower fixing knob configured to bind the first lower slot 112 and the second lower slot 122.

The insert 132 of the fixing knob 130 may include a magnetic body and a cover formed of a flexible material and configured to cover the magnetic body. The insert 132 may move in a longitudinal direction of the first slot and the second slot. The upper fixing knob and the lower fixing knob may be disposed perpendicular to the longitudinal direction of the first upper slot 111 and the first lower slot 112, respectively.

The linear potentiometer 140 may be, for example, a variable resistor of which a resistance value changes due to an external magnetic field. The resistance value of the linear potentiometer 140 may vary based on a location of the magnetic body included in the insert 132. Since the linear potentiometer 140 is disposed between the first upper slot 111 and the first lower slot 112, the resistance value may change due to an influence of a magnetic field of the magnetic body in the insert 132.

In an example of FIG. 3, a width of the fixing module 20 may be minimized when the fixing knob 130 passes through a left end of the first slot and simultaneously passes through a right end of the second slot. Also, the width of the fixing module 20 may be maximized when the fixing knob 130 passes through a right end of the first slot and simultaneously passes through a left end of the second slot.

In this example, a length adjustment range may be determined in advance since the first side frame 110 and the second side frame 120 are provided in a curved form to cover the waist of the user. Thus, the fixing module 20 may be set to have a minimum width when the fixing knob 130 passes through a left end of the first slot and simultaneously passes through a right end of the second slot the fixing knob 130. Also, the fixing module 20 may be set to have a maximum width when the fixing knob 130 passes through a right end of the first slot and simultaneously passes through a left end of the second slot.

When a binding member, for example, the fixing knob 130 is disposed adjacent to the left end of each of the first upper slot 111 and the first lower slot 112, an area between the first side frame 110 and the second side frame 120 may be minimized and the linear potentiometer 140 may have a minimum resistance value.

The controller 60 may include a memory and a processor (not shown).

The memory may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The processor may be implemented by at least one semiconductor chip disposed on a printed circuit board. The processor may be an arithmetic logic unit, a digital signal processor, a microcomputer, a field programmable array, a programmable logic unit, a microprocessor or any other device capable of responding to and executing instructions in a defined manner.

The processor may be programmed with instructions that configure the processor into a special purpose computer to perform the operations illustrated in FIG. 9, discussed below, such that the processor is configured to determine the width W of the waist of user, and to determine the driving torque T based on the width W of the user. For example, the processor may adjust one or more of the amplitude and phase of a torque pattern based on the width W of the user.

The controller 60 may receive information on the minimum resistance value, and decrease a driving torque T of the driving module 30 to be a minimum torque Tmin which is a smallest torque to be applied by the driving module 30 to generate a movement of the user.

When the fixing knob 130 is disposed adjacent to the right end of each of the first upper slot 111 and the first lower slot 112, the area between the first side frame 110 and the second frame 120 may be maximized and the linear potentiometer 140 may have a maximum resistance value. The controller 60 may receive information on the maximum resistance value, and increase the driving torque T of the driving module 30 to be a maximum torque Tmax which is a greatest torque to be applied by the driving module 30 for the movement of the user.

When the fixing knob 130 is disposed between the left end and the right end of the first upper slot 111 or the first lower slot 112, the linear potentiometer 140 may have an intermediate value between the minimum resistance value and the maximum resistance value. Thus, the controller 60 may receive information on the intermediate resistance value, and determine the driving torque T of the driving module 30 to be a torque between the minimum torque Tmin and the maximum torque Tmax.

A width between the first side frame 110 and the second side frame 120 may be adjusted by increasing or decreasing a space between curved center portions of the first side frame 110 and the second side frame 120 provided in a mirror symmetry form relative to the first side frame 110.

Figure 4:
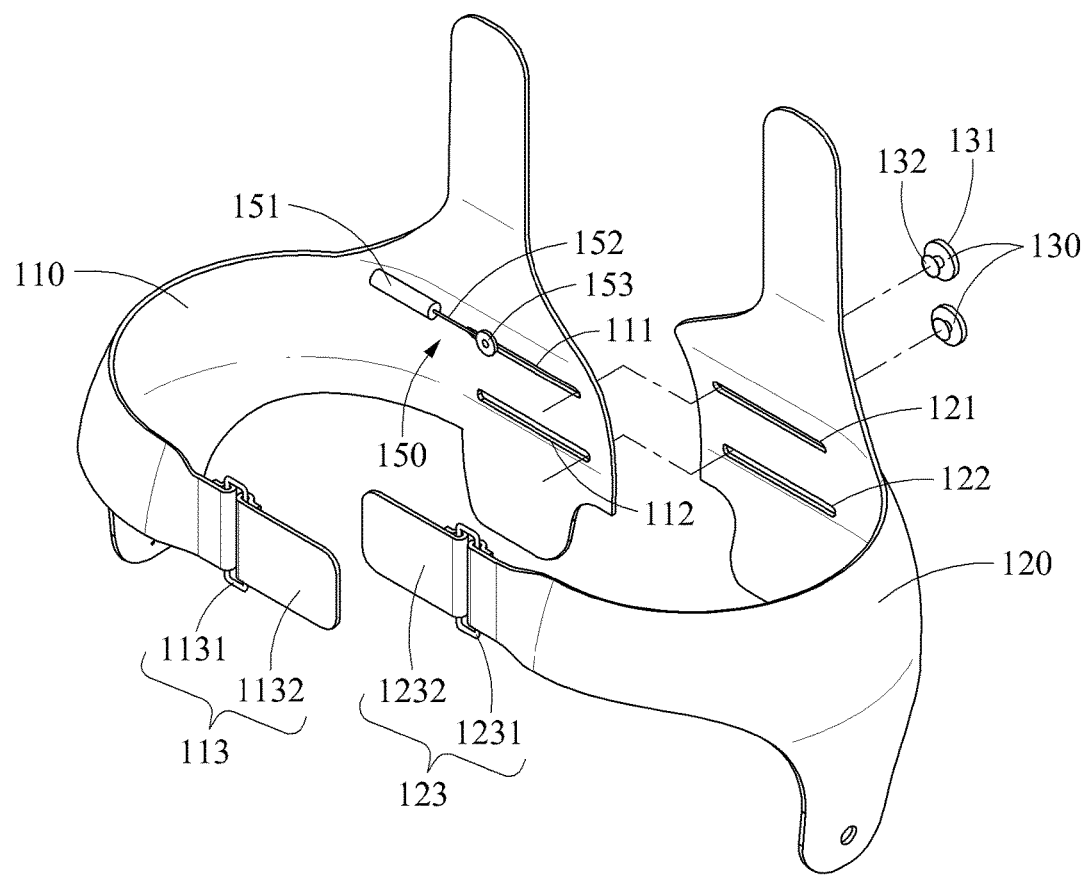
FIG. 4 is a perspective view illustrating a fixing module including a linear variable differential transformer (LVDT) sensor.

FIG. 4 is a perspective view illustrating a fixing module including a linear variable differential transformer (LVDT) sensor.

Referring to FIG. 4, the fixing module 20 may include a linear variable differential transformer (LVDT) sensor 150. The foregoing descriptions related to the elements included in the first side frame 110 and the second side frame 120 of FIG. 3 may also be applicable to the example of FIG. 4.

The LVDT sensor 150 may include a core 152 provided in a beam or cylindrical form and a main body 151 to which the core 152 is inserted. The main body 151 may be electrically connected to the controller 60. One end of the core 152 may be inserted in the main body 151, and a receiver 153 may be attached to another end of the core 152.

The LVDT sensor 150 may be fixed to the first side frame 110. The main body 151 may be fixed to a left portion close to a first upper slot 111 in the first side frame 110. The main body 151 may be disposed such that a longitudinal direction of the main body 151 is on a line extended in a longitudinal direction of the first upper slot 111.

The core 152 may move in and out of the main body 151. A moving direction of the core 152 may match the longitudinal direction of the first upper slot 111. The receiver 153 may be synchronized with a movement of the core 152. The insert 132 of the fixing knob 130 may be inserted to a center hole of the receiver 153 by passing through the first upper slot 111 and the second upper slot 112.

A displacement value measured by the main body 151 may vary based on a degree to which the core 152 is inserted into the main body 151. When a width of the first side frame 110 and the second side frame 120 is minimized, the receiver 153 may be located at a left end of the first upper slot 111. The main body 151 may transmit location information of the receiver 153 to the controller 60, and the controller 60 may adjust the driving torque to be a minimum torque.

In contrast, when the width of the first side frame 110 and the second side frame 120 is maximized, the receiver 153 may be located at a right end of the first upper slot 111. The main body 151 may transmit location information of the receiver 153 to the controller 60, and the controller 60 may adjust the driving torque T to a maximum torque Tmax.

In general, a waist width of a user may be proportional to a weight of the user. Thus, it is possible to prevent the user from experiencing inconvenience by determining a torque improved (or, alternatively, optimized) based on a body of the user to be less than the maximum torque Tmax applicable by the driving module 30 through a width measurement of the fixing module 20, and providing a motion assistance to the user based on the determined torque.

As an example, when a user is pregnant or suffers from abdominal obesity, a required intensity of driving torque may be less than that of a common user despite a relatively large waist width. As another example, when a user has muscle mass greater than that of a common user, a required intensity of driving torque may greater than that of the common user despite a relatively slight increase in a waist width. Thus, a degree to which a driving torque is proportional to a waist width may be differently set based on a condition of a user. When a user has trouble with using an information technology (IT) device and the user is unable to receive assistance for utilizing the motion assistance apparatus 10, the driving torque T may be intuitively adjusted using a width corresponding to a mechanical measurement, in lieu of a user-customized setting based on a complex user interface (UI).

FIGS. 5A through 5D illustrate examples of a torque pattern of a driving torque T.

Figure 5A:
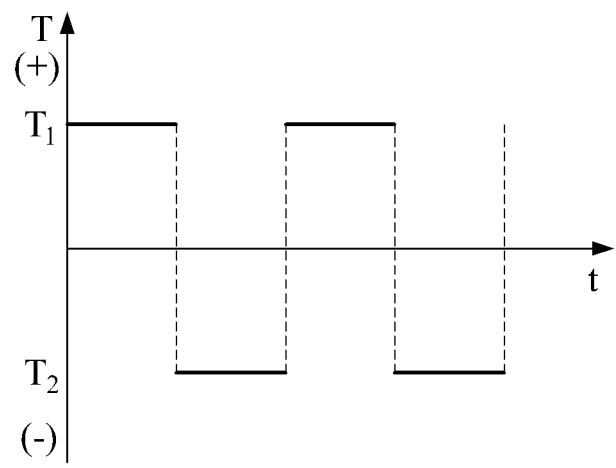
FIGS. 5A through 5D illustrate examples of a torque pattern of a driving torque T.
Figure 5B:
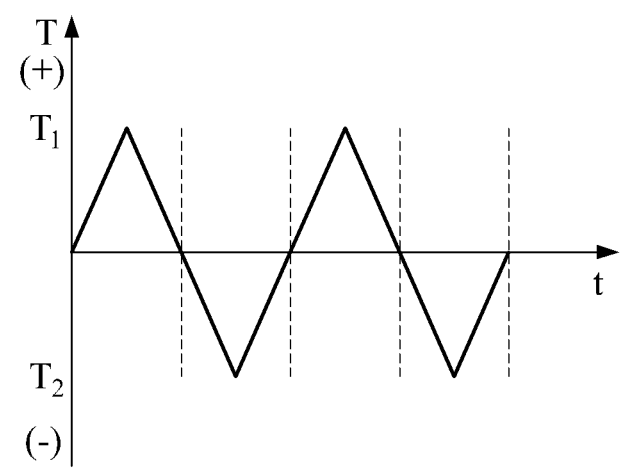
Figure 5C:
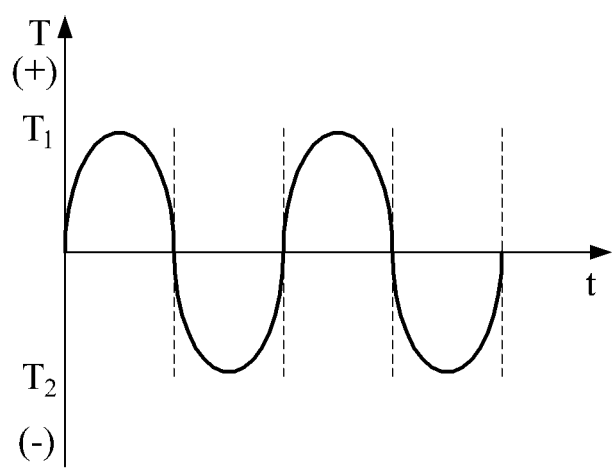
Figure 5D:
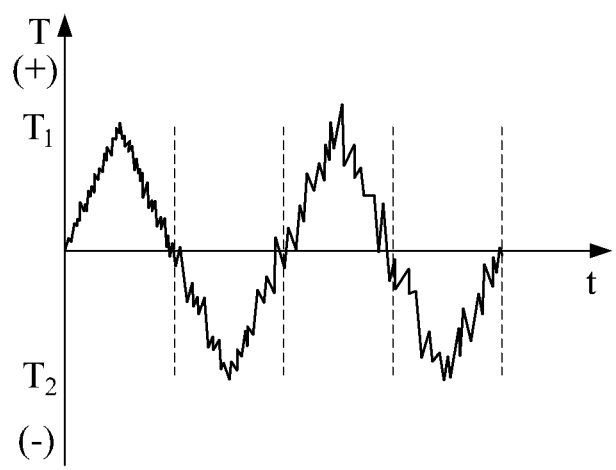

Referring to FIGS. 5A to 5D, FIG. 5A illustrates a torque pattern in a form of a step function having constant values when the leg is lifted and landed. FIG. 5B illustrates a torque pattern in a form of a wedge function in which a form of a linear function is repeated. FIG. 5C illustrates a torque pattern in a form of a sine wave. FIG. 5D illustrates a torque pattern in which an irregular form is repeated.

Rotation power of the driving module 30 may include the driving torque T transmitted from the driving module 30 to the supporting module 50. A minimum torque Tmin may indicate a smallest torque to be applied by the driving module 30 to generate a movement of the user and a maximum torque Tmax indicates a greatest torque to be applied by the driving module 30 for the movement of the user.

The driving torque T may have a torque pattern in which a desired (or, alternatively, a predetermined) form is repetitively provided, in lieu of continually having the same value. In FIGS. 5A through 5D while the user is wearing the motion assistance apparatus 10, the driving torque T applied to lift a leg of the user may have a positive (+) value and the driving torque T applied to land the leg on a ground may have a negative (−) value.

The controller 60 may determine an amplitude of a torque pattern corresponding to a maximum value of an absolute value of the driving value T to be between the minimum torque Tmin and the maximum torque Tmax. For example, the controller 60 may adjust values of T1 and T2 for each graph of FIGS. 5A through 5D separately based on the width measurement of the fixing module 20. Also, the controller 60 may change a phase of the torque pattern, and adjust the torque pattern by increasing or decreasing a period of time during which the torque pattern appears.

Figure 6:
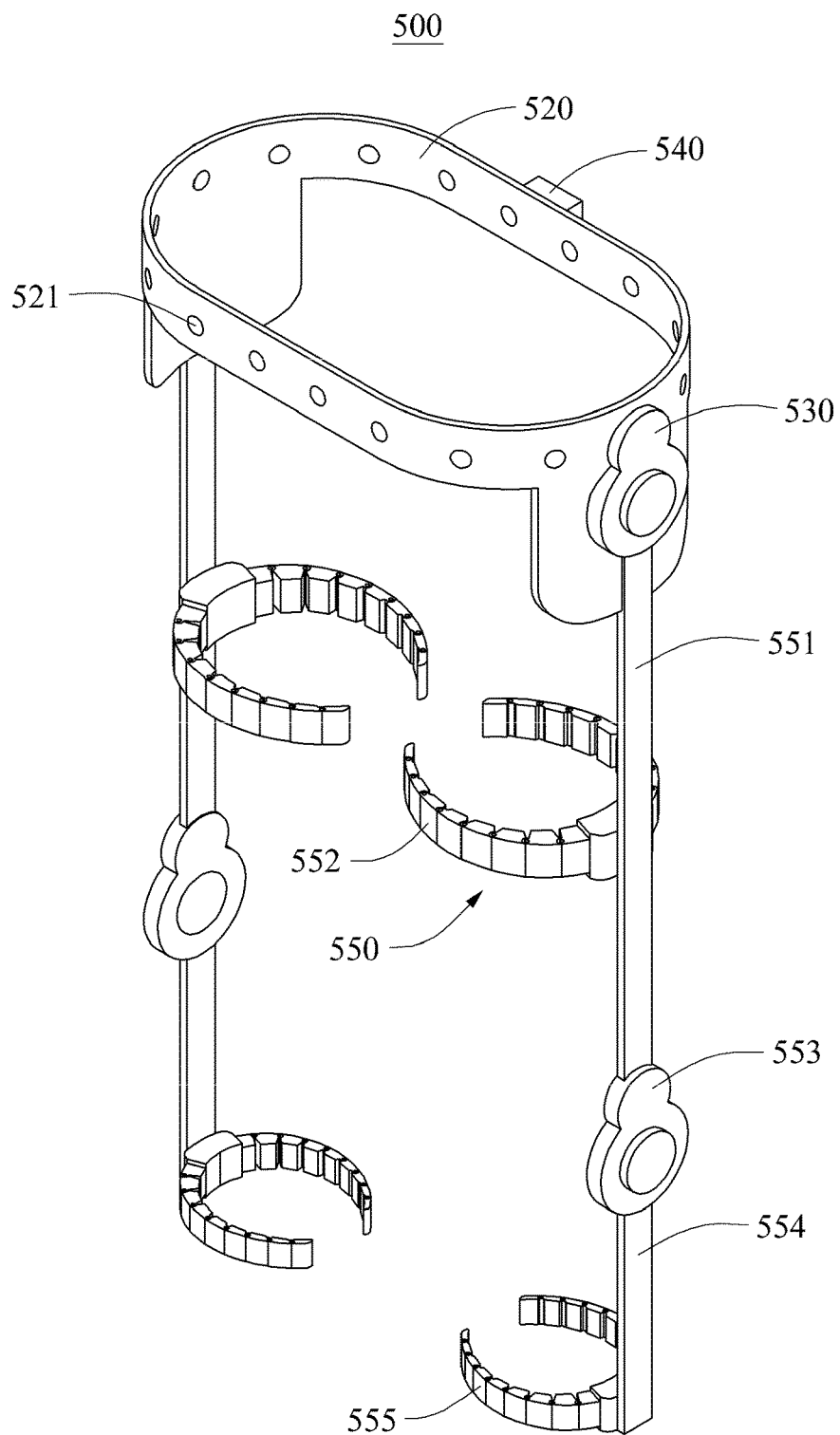
FIG. 6 is a perspective view illustrating an example of a motion assistance apparatus according to other example embodiments.
Figure 7:
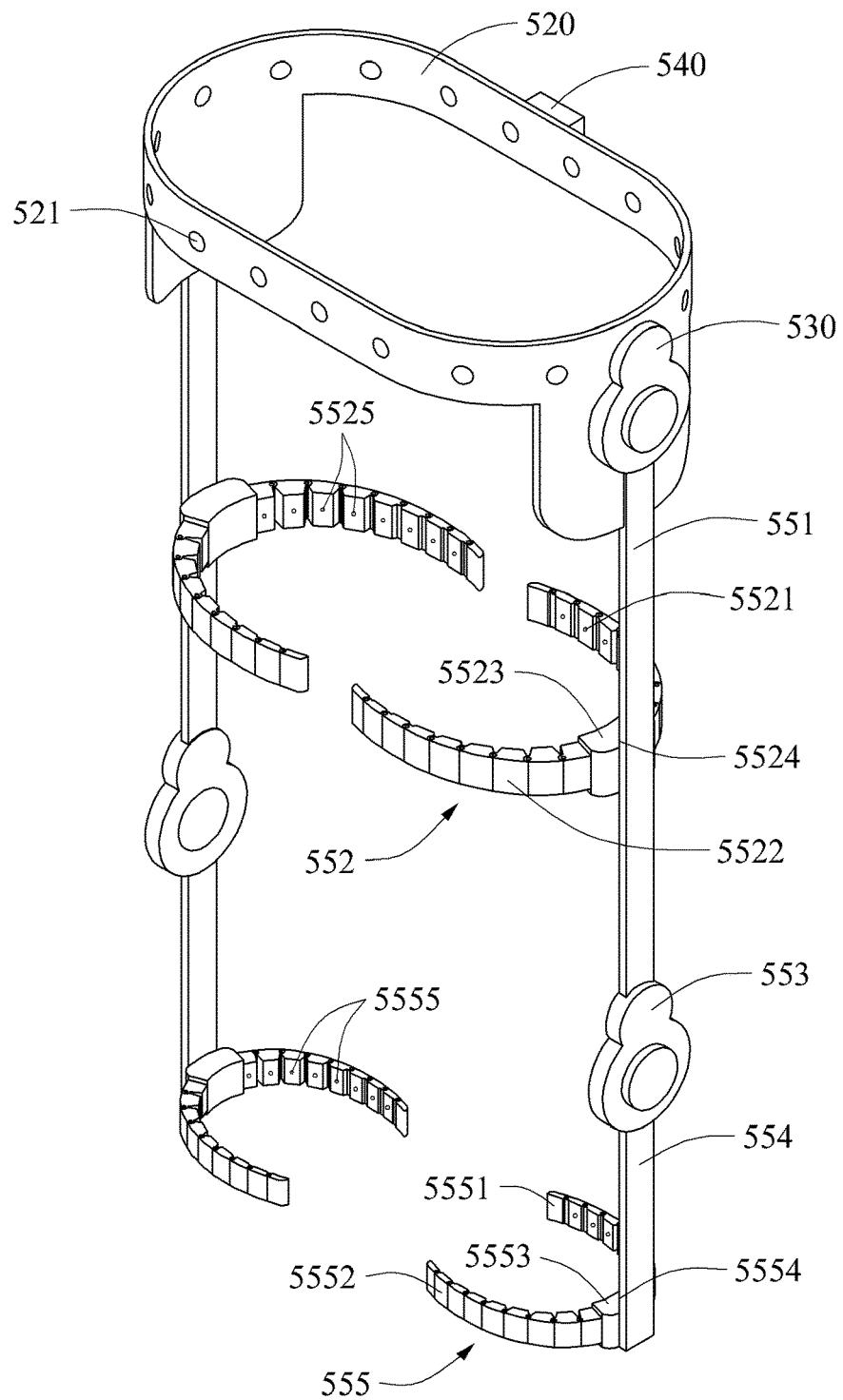
FIG. 7 is a perspective view illustrating an example of a supporting module in a motion assistance apparatus.

FIGS. 6 and 7 illustrate examples of a motion assistance apparatus according to other example embodiments.

Referring to FIGS. 6 and 7, a motion assistance apparatus 500 may be provided in a form differing from that of the motion assistance apparatus 10. For example, in the motion assistance apparatus 500, a supporting module 550 may support an entire leg of a user and/or include sensors to measure the width of various portions of the user's leg.

The motion assistance apparatus 500 may include a fixing module 520 attached to a portion of the user, a driving module 530 rotatably fixed to the fixing module 520, and the supporting module 550 configured to support the entire leg of the user and driven by the driving module 530.

The fixing module 520 may include a waist measurement sensor 521 configured to measure a waist size of the user. The supporting module 550 may include a sensor configured to measure a thigh size and a calf size of the user. A controller 540 may adjust rotation power of the driving module 530 based on a body size of the user measured in a sensor module including the aforementioned sensors.

The waist measurement sensor 521 may include a plurality of location sensors disposed along a circumference of the fixing module 520. The waist measurement sensor 521 may transmit location information of each sensor to the controller 540. Based on the location information, the controller 540 may obtain the waist size of the user.

The supporting module 550 may include a thigh supporting body 551, a calf supporting body 554, and a connecting joint 553. The connecting joint 553 may be disposed on a rear side of a knee of the user and configured to connect the thigh supporting body 551 and the calf supporting body 554.

The thigh supporting body 551 may include a thigh supporting frame 552 configured to support the thigh of the user by covering the thigh through a spreading or pressing-together motion. The calf supporting body 554 may include a calf supporting frame 555 configured to support the calf of the user by covering the calf.

The thigh supporting frame 552 may include a joint portion including a right joint portion 5522 and a left joint portion 5521, a joint connector 5523 configured to connect the right joint portion 5522 and the left joint portion 5521, and an adjusting member 5524 disposed on a rear side of the joint connector 5523 and configured to adjust a degree to which the right joint portion 5522 and the left joint portion 5521 are spread or pressed together. The calf supporting frame 555 may include a joint portion including a right joint portion 5552 and a left joint portion 5551, a joint connector 5553 configured to connect the right joint portion 5552 and the left joint portion 5551, and an adjusting member 5554 disposed on a rear side of the joint connector 5553 and configured to adjust a degree to which the right joint portion 5552 and the left joint portion 5551 are spread or pressed together.

A plurality of thigh measurement sensors 5525 configured to measure the thigh size of the user may be disposed on an inner side surface of the joint portion in the thigh supporting frame 552. A plurality of calf measurement sensors 5555 configured to measure the calf size of the user may be disposed on an inner side surface of the joint portion in the calf supporting frame 555.

The thigh measurement sensor 5525 may be a location sensor disposed on an inner surface of a link configuring the joint portion of the thigh supporting frame 552. The calf measurement sensor 5555 may be a location sensor disposed on an inner surface of a link configuring the joint portion of the calf supporting frame 555.

The thigh measurement sensor 5525 and the calf sensor 5555 may be included on the thigh support 552 and the calf support 555, respectively, associated with one or more the left leg and the right leg of the user. For example, in some example embodiments, to reduce cost and weight, the thigh measurement sensor 5525 and the calf sensor 5555 may only be included on supports of one of the left leg and the right leg of the user.

The thigh measurement sensor 5525 and the calf measurement sensor 5555 may transmit location information of each sensor to the controller 540. Based on the location information, the controller 540 may obtain the thigh size and the calf size of the user.

The controller 540 may include a memory and a processor (not shown).

The memory may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The processor may be implemented by at least one semiconductor chip disposed on a printed circuit board. The processor may be an arithmetic logic unit, a digital signal processor, a microcomputer, a field programmable array, a programmable logic unit, a microprocessor or any other device capable of responding to and executing instructions in a defined manner.

The processor may be programmed with instructions that configure the processor into a special purpose computer to perform the operations illustrated in FIG. 10, discussed below, such that the processor is configured to determine the size L of the user, and to determine the driving torque T based on the size L of the user. For example, the processor may adjust one or more of the amplitude and phase of a torque pattern based on the size L of the user.

The controller 540 may obtain one size L of the user based on the location information measured by the waist measurement sensor 521, the thigh measurement sensor 5525, and the calf measurement sensor 5555. The controller 540 may compare the one size L and a maximum size Lmax.

The rotation power adjusted by the controller 540 may include a driving torque T. In terms of the driving torque T, a minimum torque Tmin may indicate a smallest torque to be applied by the driving module 530 to generate a movement of the user and a maximum torque Tmax indicates a greatest torque to be applied by the driving module 530 for the movement of the user. The controller 540 may determine the driving torque T to be a torque between the minimum torque Tmin and the maximum torque Tmax such that the driving torque is proportional to the one size L of the user.

Figure 8:
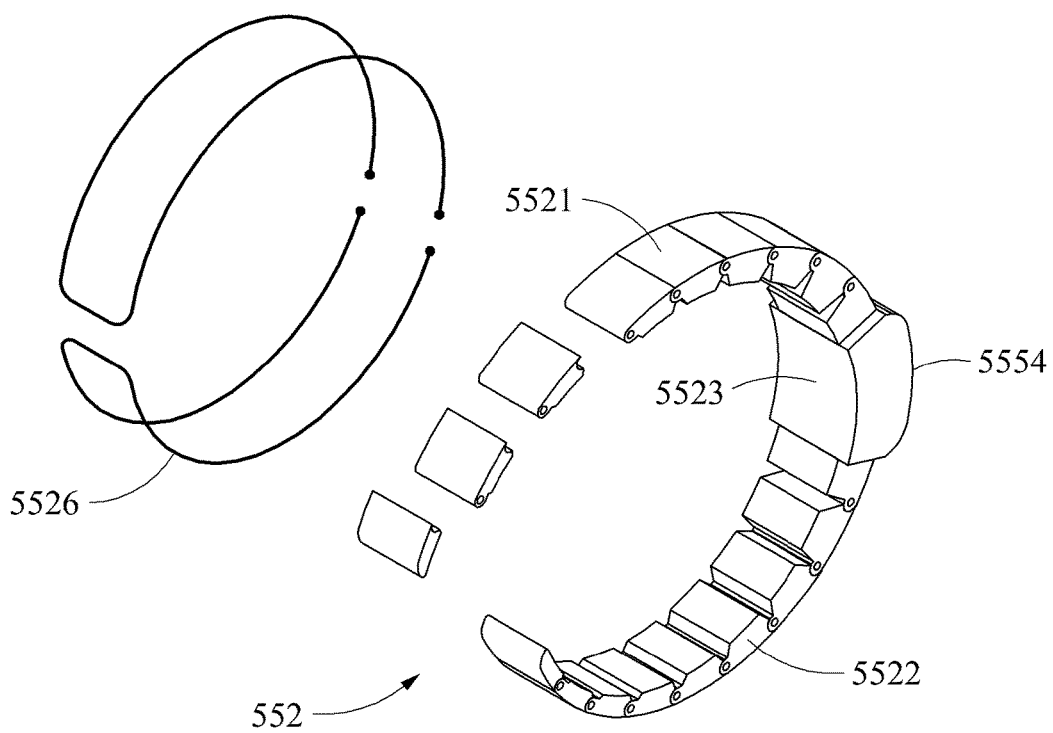
FIG. 8 is an exploded perspective view illustrating an example of a supporting frame in a supporting module.

FIG. 8 is an exploded perspective view illustrating the thigh supporting frame 552 of the supporting module 555.

Referring to FIG. 8, the thigh supporting frame 552 may include the left joint portion 5521, the right joint portion 5522, the joint connector 5523 configured to connect the left joint portion 5521 and the right joint portion 5522, and the adjusting member 5524 disposed on the rear side of the joint connector 5523 and configured to adjust a degree to which the left joint portion 5521 and the right joint portion 5522 are spread or pressed together.

Each of the left joint portion 5521 and the right joint portion 5522 may include a plurality of links, a shaft configured to connect the links to each other, and a wire 5526 passing through the links. The wire 5526 may be wound or unwound by the adjusting member 5524.

When the wire 5526 is wound by the adjusting member 5524, to compensate for a portion of the wire 5526 passing through the links decreasing in length, an angle between the links of the left joint portion 5521 and the right joint portion 5522 may decrease. In response to a decrease in the angle, the left joint portion 5521 and the right joint portion 5522 may be pressed together to cover a leg of the user. Conversely, when the wire 5526 is unwound by the adjusting member 5524, to compensate for a portion of the wire 5526 passing through the links increasing in length, the angle between the links of the left joint portion 5521 and the right joint portion 5522 may increase. In response to an increase in the angle, the left joint portion 5521 and the right joint portion 5522 may be spread and detached from the leg of the user.

The adjusting member 5524 may be included in a cover configured to cover the joint connector 5553, and configured to automatically or manually wind and unwind the wire 5526. To allow the user to manually wind the wire 5526, the adjusting member 5524 may include a gear used to wind the wire 5526 and a joint knob used to rotate the gear.

The adjusting member 5524 may include the gear to wind the wire 5526 and a servo motor connected to a controller and rotate the gear. When the user wears the thigh supporting frame 552, the controller may allow the left joint portion 5521 and the right joint portion 5522 to be automatically pressed together.

When the left joint portion 5521 and the right joint portion 5522 are pressed together, the controller may measure the thigh size of the user using a plurality of location sensors included in the links for each of the left joint portion 5521 and the right joint portion 5522.

The foregoing descriptions related to the thigh supporting frame 552 may also be applicable to the calf supporting frame 555. In terms of the calf supporting frame 555, for example, a thigh size of a user may be larger than a general calf size. Thus, the number of links included in the thigh supporting frame 552 may be larger than the number of links included in the calf supporting frame 555, and a wire of the thigh supporting frame 552 may be longer than a wire of the calf supporting frame 555.

Figure 9:
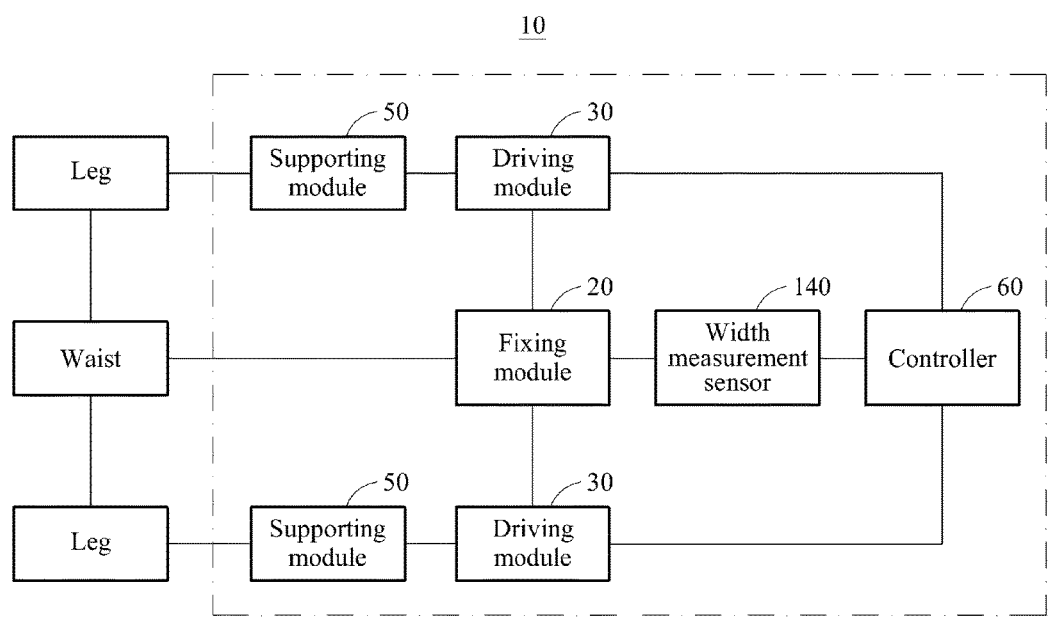
FIG. 9 is a view illustrating an example of a configuration of a motion assistance apparatus.

FIG. 9 illustrates a configuration of the motion assistance apparatus 10.

Referring to FIGS. 1-4 and 9, in the motion assistance apparatus 10, the controller 60 may control the driving torque T of the driving module 30 and receive width information of the fixing module 20 measured by the width measurement sensor 140 attached to the fixing module 20. The fixing module 20 may be attached to the user by covering a waist of a user.

Two driving modules 30 may be provided on both sides of the fixing module 20. The driving modules 30 may be connected to two supporting modules 50, each configured to support a leg or part of a leg, for example, a thigh of the user. The supporting modules 50 may support a right leg and a left leg of the user. The controller 60 may control the respective driving modules 30.

A width of the fixing module 20 may be substantially the same as a distance between two driving modules 30. Also, the width of the fixing module 20 may be adjustable. An adjusted width may be consistently measured by the width measurement sensor 140, thereby adjusting the driving torque T of the driving module 30.

Figure 10:
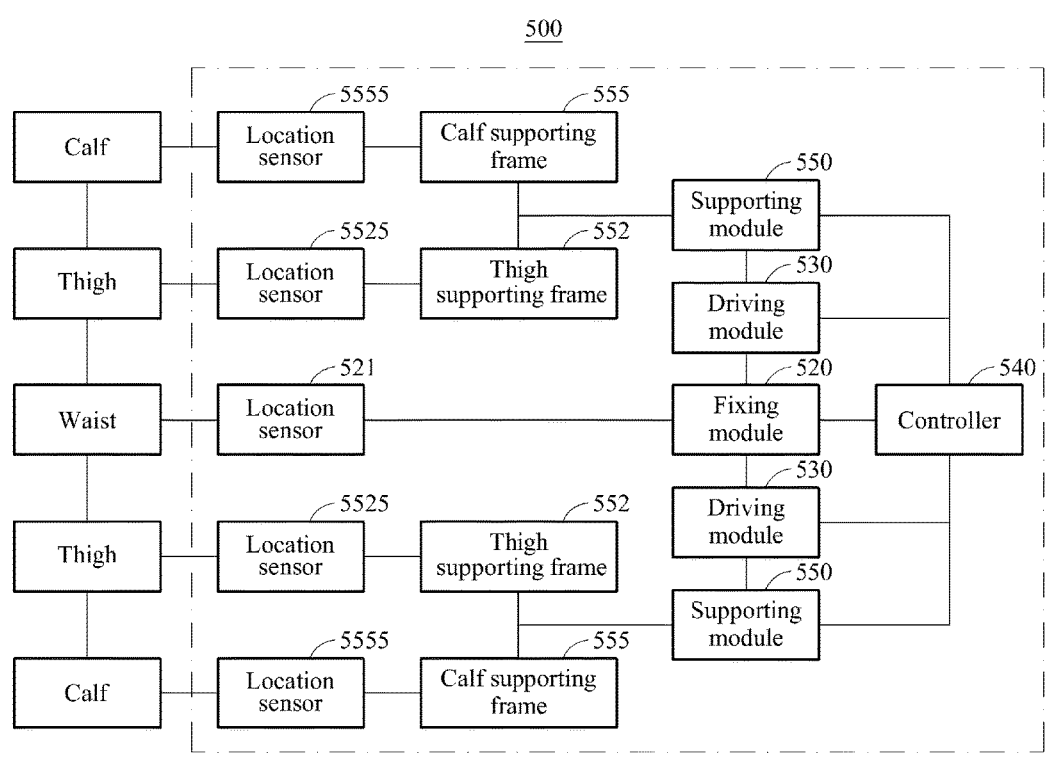
FIG. 10 is a view illustrating another example of a configuration of a motion assistance apparatus.

FIG. 10 illustrates a configuration of the motion assistance apparatus 500.

Referring to FIGS. 6 and 10, in the motion assistance apparatus 500, the controller 540 may control the driving torque T of the two driving modules 530 attached to two fixing modules 520.

The fixing module 520 may be attached to a waist of a user by covering the waist of the user, and a plurality of location sensors 521 may be disposed on the fixing module 520 to measure a waist size of the user. Each of the plurality of location sensors 521 may measure location information and transmit the measured location information to the controller 540. The controller 540 may calculate the waist size of the user based on the location information.

The driving module 530 may be connected with the thigh supporting frame 552 configured to support a thigh of the user and the calf supporting frame 555. The location sensor 5525 may be disposed on the thigh supporting frame 552 to measure a thigh size, for example, a circumference of the thigh and the location sensor 5555 may be disposed on the calf supporting frame 555 to measure a calf size.

The controller 540 may receive location information from the location sensor 521 disposed on the fixing module 520, and the location sensors 5525 and 5555 disposed on the supporting module 550. Based on the received location information, the controller 540 may obtain information on a waist size, the thigh size, and the calf size of the user. The controller 540 may obtain one size of the user based on the waist size, the thigh size, and the calf size, and adjust an intensity of the driving torque applied by the driving module 530 to the supporting module 550.

Figure 11:
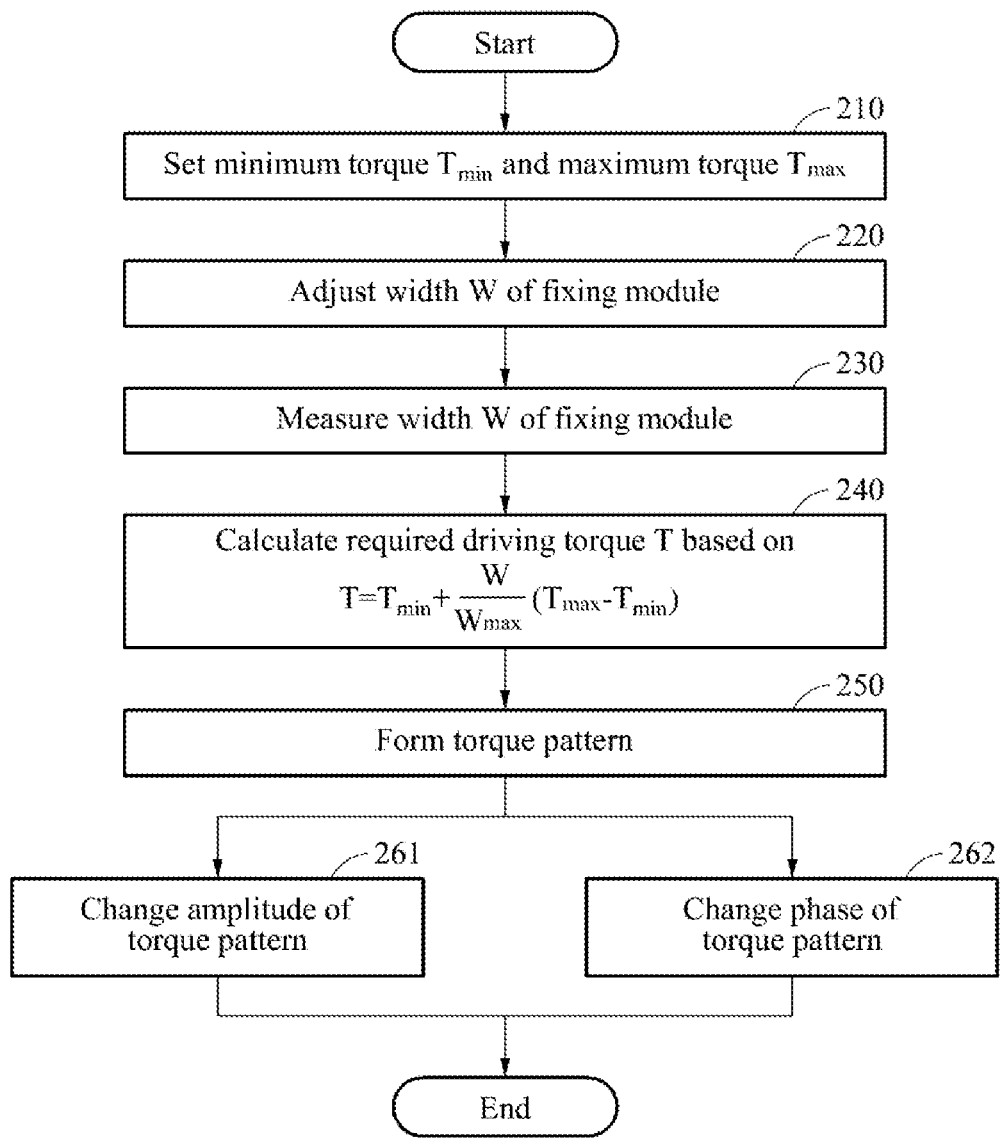
FIG. 11 is a flowchart illustrating an example of a method of controlling a motion assistance apparatus.

FIG. 11 is a flowchart illustrating an example of a method of controlling the motion assistance apparatus 10 according to some example embodiments.

Referring to FIGS. 1-4, 9 and 11, the motion assistance apparatus 10 may include the fixing module 20 attached to a portion of the user, the driving module 30 attached to the fixing module 20 to generate rotation power, the supporting module 50 configured to support another portion of the user and driven by the driving module 30, and the controller 60 configured to control the driving module 30. Also, the motion assistance apparatus 10 may be worn by the user.

In operation 210, the controller 60 may set a minimum torque Tmin indicating a smallest torque to be applied by the driving module 30 to generate a movement of the user and a maximum torque Tmax indicating a greatest torque to be applied by the driving module 30 for the movement of the user. In some example embodiments, operation 210 may be performed in advance and/or preset. In other example embodiments, operation 210 may be performed by the controller 60 at runtime.

In operation 220, the user may adjust a width of the fixing module 20. In some example embodiments, the user may manually adjust a width W of the fixing module 20 using a fixing knob. In other example embodiments, the controller 60 may automatically adjust the width W of the fixing module 20 using a servo motor when the user wears the motion assistance apparatus 10.

In operation 230, a sensor may measure the width W of the fixing module 20 when the user wears the motion assistance apparatus 10. The measured width W may be less than or equal to a maximum width Wmax.

In operation 240, the controller 60 may calculate the required driving torque T based on the measured width W using Equation 1 as shown below.

$$T = T_{min} + \frac{W}{W_{max}} \cdot (T_{max} - T_{min}) \qquad \text{[Equation 1]}$$

In Equation 1, $$\frac{W}{W_{max}}$$

denotes a ratio in width, $T_{min}$ denotes a maximum torque indicating a value of the driving torque T calculated when the measured width W is the maximum width $W_{max}$ to be adjusted, and the value of the driving torque T may increase as a torque between the minimum torque $T_{min}$ and the maximum torque $T_{max}$ proportionally to the measured width W in a form of a linear function.

In operation 250, the controller 60 may form a torque pattern of the driving torque T. The torque pattern may be represented in a desired (or, alternatively, a predetermined) form as illustrated in FIGS. 5A to 5D. Also, the controller 60 may individually determine different torque pattern s for a right leg and a left leg.

In operation 261, the controller 60 may adjust an amplitude of the torque pattern to be a torque between the minimum torque Tmin and the maximum torque Tmax based on Equation 1. In this example, the torque pattern may be, for example, a maximum value of an absolute value of the driving torque T.

In operation 262, the controller 60 may change a phase of the torque pattern to delay or advance a pattern appearance time.

FIG. 12 is a flowchart illustrating another example of a method of controlling the motion assistance apparatus 500.

Referring to FIGS. 6-8, 10 and 12, the motion assistance apparatus 500 may include the fixing module 520 attached to a waist of the user, the driving module 530 attached to the fixing module 520 to generate rotation power, the supporting module 550 configured to support an entire leg of the user and driven by the driving module 530, and the controller 540 configured to control the driving module 530. Also, the motion assistance apparatus 500 may be worn by the user. The supporting module 550 may be configured to support the entire leg of the user and include the calf supporting frame 555 and the thigh supporting frame 552.

The fixing module 520 may include a sensor 521 configured to measure a waist size. The calf supporting frame 555 may include a sensor 5555 configured to measure a calf size. The thigh supporting frame 552 may include a sensor 5525 configured to measure a thigh size.

In operation 610, the controller 540 may set a minimum torque Tmin indicating a smallest torque to be applied by the driving module 30 to generate a movement of the user, and a maximum torque Tmax indicating a greatest torque to be applied by the driving module 30 for the movement of the user.

In operation 621, the location sensor 521 of the fixing module 520 may transmit location information measured by each location sensor to the controller 540, and the controller 540 may measure a waist size of the user.

Simultaneously, in operation 622, the location sensor 5525 of the thigh supporting frame 552 may measure a thigh size of the user, and the location sensor 5555 of the calf supporting frame 555 may measure a calf size of the user.

In operation 630, the controller 540 may obtain one size L of the user based on the measured waist size, calf size, and thigh size. The one size L may relate to a weight of the user. In terms of the one size L, a maximum acceptable size of the user may be determined as a maximum size Lmax in advance, and the determined size may be less than or equal to the maximum size Lmax.

In operation 640, the necessary driving torque T may be calculated based on the one size L using Equation 2 as shown below.

$$T = T_{min} + \frac{L}{L_{max}} \cdot (T_{max} - T_{min}) \quad \text{[Equation 2]}$$

In Equation 2, Tmin denotes a maximum torque indicating a value of the driving torque T calculated when the one size L is the maximum size Lmax, and the value of the driving torque T may increase to be a torque between the minimum torque Tmin and the maximum torque Tmax proportionally to the one size L in a form of a linear function.

In operation 650, the controller 540 may form a torque pattern of the driving torque T. The torque pattern may be represented in a predetermined form as illustrated in FIG. 5. Also, a torque pattern of a right leg may differ from a torque pattern of a left leg.

In operation 661, the controller 540 may adjust an amplitude of the torque pattern to be a torque between the minimum torque Tmin and the maximum torque Tmax based on Equation 2. In this example, the torque pattern may be, for example, a maximum value of an absolute value of the driving torque T.

In operation 662, the controller 540 may change a phase of the torque pattern to delay or advance a pattern appearance time.

The units and/or modules described herein may be implemented using hardware components and software components. For example, the hardware components may include microphones, amplifiers, band-pass filters, audio to digital converters, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciate that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A motion assistance apparatus comprising:
a fixing device attached to a user;
a driver configured to generate rotation power;
a support configured to support a portion of a body of the user and rotate in response to the rotation power;
a sensor configured to measure a width of the fixing device; and
a controller configured to adjust the rotation power based on the measured width.

2. The apparatus of claim 1, wherein the rotation power includes a driving torque transmitted from the driver to the support, and
the controller is configured to determine the driving torque between a minimum driving torque and a maximum torque based on the measured width.

3. The apparatus of claim 2, wherein the controller is configured to determine the driving torque based on:

$$T = T_{min} + \frac{W}{W_{max}} \cdot (T_{max} - T_{min})$$

where T denotes the driving torque, $T_{min}$ denotes the minimum driving torque, $T_{max}$ denotes the maximum driving torque, W denotes the width of the fixing device, and $W_{max}$ denotes a maximum width of the fixing device.

4. The apparatus of claim 2, wherein the controller is configured to set an amplitude of a torque pattern between the minimum torque $T_{min}$ and the maximum torque $T_{max}$ and apply the set torque pattern as the driving torque.

5. The apparatus of claim 1, wherein the fixing device comprises:
a width adjuster configured to adjust the width of the fixing device, wherein
the sensor is connected to the width adjuster.

6. The apparatus of claim 5, wherein
the fixing device includes a first side frame configured to enclose a first side of the user and a second side frame configured to enclose a second side of the user, and
the width adjuster includes a fixing knob configured to fix the first side frame and the second side frame by passing through a first slot and a second slot in the first side frame and the second side frame, respectively such that the width of the fixing device decreases according to an increase in an overlapping portion between the first side frame and the second side frame.

7. The apparatus of claim 6, wherein the sensor comprises:
a linear potentiometer including,
a variable resistor having a first side and a second side, the first side connected to the controller and the second side connected to one of the first side frame and the second side frame, and
a magnetic body connected to the fixing knob, the magnetic body configured to change a resistance value of the variable resistor based on a location of the magnetic body.

8. The apparatus of claim 7, wherein the variable resistor is connected to the one of the first side frame and the second side frame and the magnetic body is connected to the fixing knob such that the variable resistor and the magnetic body are on one side of the first slot and the second slot, respectively.

9. The apparatus of claim 6, wherein the sensor comprises:
a linear variable differential transformer (LVDT) sensor including,
a core connected to the fixing knob, and
a main body connected to one of the first side frame and the second side frame, the main body configured to transmit width data to the controller.

10. The apparatus of claim 9, wherein
the core is configured to move relative to the main body such that a penetration amount the core penetrates the main body varies based on a width of the fixing device, and
the main body is configured generate the width data based on the penetration amount.

11. A method of controlling a motion assistance apparatus, the method comprising:
measuring, by a sensor mounted on a fixing device attached to a first portion of the user, a width of the fixing device; and
adjusting, by a controller, a rotation power of a driver based on the measured width, the driver configured to drive a support configured to support a second portion of the user.

12. The method of claim 11, wherein the adjusting comprises:

determining the rotation power based on the following equation:

$$T = T_{min} + \frac{W}{W_{max}} \cdot (T_{max} - T_{min})$$

where T denotes a driving torque associated with the rotation power, $T_{min}$ denotes a minimum driving torque, $T_{max}$ denotes a maximum driving torque, W denotes the measured width of the fixing device, and $W_{max}$ denotes a maximum width of the fixing device.

* * * * *